(12) United States Patent
Noirot et al.

(10) Patent No.: US 8,598,249 B2
(45) Date of Patent: Dec. 3, 2013

(54) PHOTOINITIATORS

(75) Inventors: Pierre-Antoine Noirot, Arenthon (FR); Thierry Marsille, Saint Pierre en Faucigny (FR); Matthieu Carni, Shanghai (CN); Gilles Catherin, Saint Genis Pouilly (FR)

(73) Assignee: Siegwerk Druckfarben AG & Co. KGaA, Siegburg (DE)

( * ) Notice: Subject to any disclaimer, the term of this patent is extended or adjusted under 35 U.S.C. 154(b) by 233 days.

(21) Appl. No.: 13/266,172

(22) PCT Filed: Apr. 19, 2010

(86) PCT No.: PCT/EP2010/055084
§ 371 (c)(1),
(2), (4) Date: Oct. 25, 2011

(87) PCT Pub. No.: WO2010/124950
PCT Pub. Date: Nov. 4, 2010

(65) Prior Publication Data
US 2012/0046377 A1 Feb. 23, 2012

(30) Foreign Application Priority Data
Apr. 30, 2009 (EP) .................................... 09159156

(51) Int. Cl.
*C08F 2/50* (2006.01)
*C08J 3/28* (2006.01)
*C07D 495/00* (2006.01)
*C07D 335/16* (2006.01)

(52) U.S. Cl.
USPC .................. 522/53; 549/13; 549/23; 549/26; 549/27

(58) Field of Classification Search
USPC ....................... 522/53; 549/27, 28, 26, 23, 13
See application file for complete search history.

(56) References Cited

U.S. PATENT DOCUMENTS

| 7,335,782 | B2 * | 2/2008 | Herlihy et al. | 549/27 |
| 7,354,957 | B2 * | 4/2008 | Herlihy | 522/53 |
| 2005/0288384 | A1 | 12/2005 | Kanke et al. | |
| 2006/0014852 | A1 | 1/2006 | Loccufier et al. | |

FOREIGN PATENT DOCUMENTS

| CN | 1546488 A | * | 11/2004 |
| CN | 1546651 A | * | 11/2004 |
| CN | 1594369 A | * | 3/2005 |
| CN | 1594370 A | * | 3/2005 |
| CN | 1594399 A | * | 3/2005 |
| CN | 1256364 C | * | 5/2006 |
| CN | 1271069 C | * | 8/2006 |
| CN | 1282664 C | * | 11/2006 |
| CN | 102241819 A | * | 11/2011 |
| JP | 2005 274923 | | 10/2005 |
| WO | 03/033492 | | 4/2003 |
| WO | 03/072567 | | 9/2003 |
| WO | 03/072568 | | 9/2003 |
| WO | 2005/021824 | | 3/2005 |

OTHER PUBLICATIONS

Jiang et al. A novel amphipathic polymeric thioxanthone photoinitiator. Polymer (2009), 50 (1), 37-41.*
Jiang et al. Polymeric photoinitiators containing in-chain thioxanthone and coinitiator amines. Macromolecular Rapid Comminications. (2004), 25(6), 748-752.*
Jiang et al. Study of Marophotoinitiators containing in-chain thioxanthone and coinitiator amines. Polymer 45(2004) 5057-5067.*
Jiang X et al.: "Study of macrophotoinitiator containing in-chain thioxanthone and coinitiator amines", Polymer, Elsevier Science Publishers B.V., GB, vol. 45, No. 15, Jul. 12, 2004, pp. 5057-5063.
Jiang X et al.: "Dendritic Macrophotoinitiator Containing Thioxanthone and Coinitiator Amine", Macromolecules, 37 (21), pp. 7850-7853, 2004.
Chen et al.: "Synthesis and Study of Novel Polyol-Bound Photosensitizers for Cationic UV-Curable Systems", Journal of Polymer Science: Part A: Polymer Chemistry, pp. 4435-4449, Wiley InterScience, Apr. 21, 2006.

* cited by examiner

*Primary Examiner* — Sanza McClendon
(74) *Attorney, Agent, or Firm* — Shoemaker and Mattare

(57) ABSTRACT

The present invention is related to novel photoinitiators, in particular to photoinitiators comprising amino groups within the molecule.

10 Claims, No Drawings

PHOTOINITIATORS

The present invention is related to novel compounds which are useful as photoinitiators in coating compositions, preferably printing inks.

Energy-curable compositions, such as UV-curable compositions, generally comprise a photoinitiator for starting/enhancing the polymerization reaction of the polymerizable material, which usually comprises ethylenically unsaturated moieties. Those photoinitiators must exhibit a good curing activity, low odour and good compatibility with the other components of the coating composition. In particular for food packaging applications, there are increasing legislative requirements a photoinitiator has to fulfil. Furthermore, the photoinitiators should be available at reasonable or low cost.

Accordingly, there has been research going on in the recent years for developing new photoinitiators meeting the above requirements. For example, in WO 03/033492, a series of photoinitiators is described.

It was the object of the present invention to provide novel photoinitiators meeting the above requirements.

This object has been solved according to the present invention by a series of photoinitiators as defined in the claims. In particular, the present invention is related to photoinitiators of the formula (I)

$(PI-Sp)_n-BB$                                                          (I)

wherein
PI is a thioxanthone moiety optionally comprising additional substituents further to the Sp moiety
Sp is a spacer unit which is selected from the group consisting of

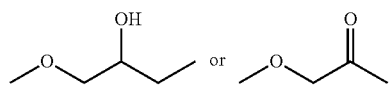

BB is a backbone moiety selected from the group consisting of

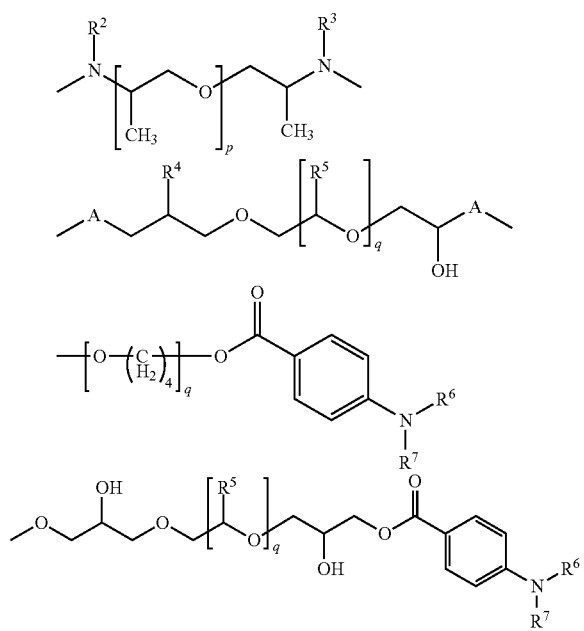

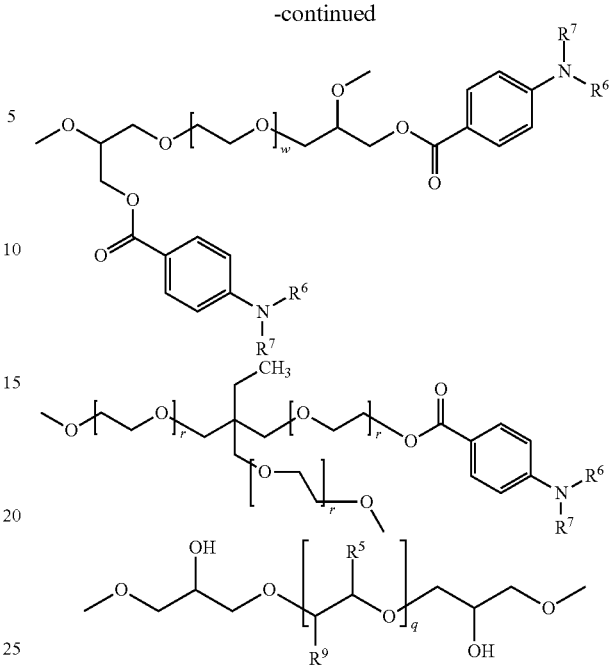

wherein
$R^2$ and $R^3$ are the same or different and denote H, an optionally substituted linear or branched $C_{1-8}$ alkyl residue or an acyl residue;
$R^4$ is H or Hydroxy;
$R^5$ is H or $C_{1-4}$-Alkyl;
$R^6$ and $R^7$ are the same or different and denote H or an optionally substituted linear or branched $C_{1-8}$ alkyl residue;
A is $NR^8$, wherein
$R^8$ is H, an optionally substituted linear or branched $C_{1-8}$ alkyl residue, or an optionally substituted $C_{1-8}$ alkylamine residue;
$R^9$ is H or $C_{1-4}$-Alkyl;
p is an integer from 1 to 10, preferably from 3 to 6;
q is an integer from 3 to 12;
r is in the range from 2 to 3;
w is an integer from 2 to 15, preferably from 3 to 10;
and
n is 1 or 2.

Throughout the application, a bond of a moiety which is not attached to an atom within said moiety shall be understood as a bond linking said moiety to a respective different moiety of the photoinitiator.

The present invention discloses new structures of photoinitiators. It has been surprisingly found that the novel compounds of the present invention are suitable photoinitiators. This could not be foreseen from the teaching of WO 03/033492 which is limited to specific structures. Thus, the present invention widely expands the range of compounds to be considered as photoinitiators in coating compositions, preferably printing inks.

According to a preferred embodiment of the present invention, it has been surprisingly found that it is also possible to insert amine groups into the backbone of the photoinitiators, and that these amine groups enhance the curing characteristics of the compounds of the present invention. Most preferably, the amine groups are tertiary amine groups. According to the present invention, the amine groups can be part of the main backbone of the compounds of the present invention, or alternatively they can be introduced into the compounds as side or terminating groups.

According to another embodiment of the present invention, novel nitrogen-free photoinitiators are also provided showing also good curing and compatibility characteristics. Those nitrogen-free photoinitiators comprise free hydroxyl groups. It has been surprisingly found that those substances still show good curing and compatibility characteristics, but can be additionally linked to a binder resin (e.g. by reaction of the free hydroxyl groups with isocyanate groups). This prevents the escape of those photoinitiators from the composition and thus avoids low odour of the composition, and minimises the risk of migration outside the coating film.

According to the present invention, PI is a thioxanthone.

According to the present invention, it has been found that the photoreactivity of the present compounds is best when the Sp moiety linking the thioxanthone moiety to the polymeric backbone is in 2-position at the thioxanthone ring.

In contrast to the teaching of WO 03/033492 it has been surprisingly found that the photoreactivity of the compounds of the invention can be enhanced if there is at least one, preferably one or two, additional substituents, beside the Sp moiety, at the PI moiety. According to a most preferred embodiment, it has been found that an additional substituent, in particular a $C_{1-4}$ alkyl moiety, preferably a methyl or isopropyl moiety, especially an isopropyl moiety, in 4 position of the thioxanthone moiety has a favourable effect.

Thus, according to a preferred embodiment of the present invention, the moiety PI is substituted with at least one, preferably one or two residues selected from the group consisting of linear or branched $C_{1-8}$ alkyl, preferably linear or branched $C_{1-4}$ alkyl, linear or branched $C_{1-8}$ alkoxy, preferably linear or branched $C_{1-4}$ alkoxy, or halogen, preferably Cl. The linear or branched $C_{1-8}$ alkyl, preferably linear or branched $C_{1-4}$ alkyl residue is particularly preferred.

The synthesis of substituted thioxanthones is known to the skilled person. Several substituted thioxanthones are commercially available.

According to a preferred embodiment of the present invention, substituted thioxanthones are manufactured by the reaction of thiosalicylic acid (commercially available from e.g. Sigma Aldrich) with respectively substituted phenol derivatives. For example, the synthesis of 2-Hydroxy-4-isopropylthioxanthon is accomplished by the following route:

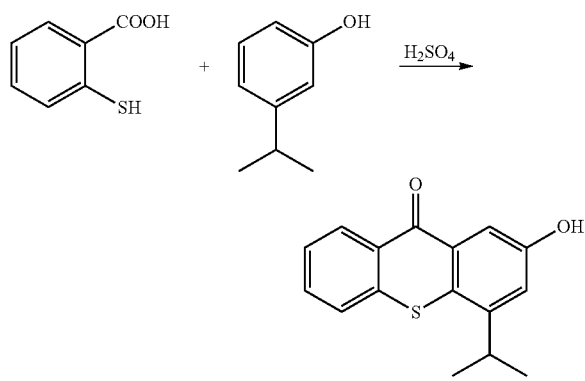

The reaction is carried out in the presence of a strong acid such as concentrated sulfuric acid under heating to about 60 to 100° C.

The spacer units can be attached to the thioxanthone or acridone moiety via well-known reactions.

The spacer unit

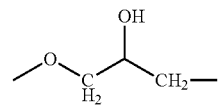

may be formed by reaction of a 2-hydroxy thioxanthone derivative with epichlorohydrine and subsequent reaction with a nucleophilic group (Nu) of the backbone unit BB:

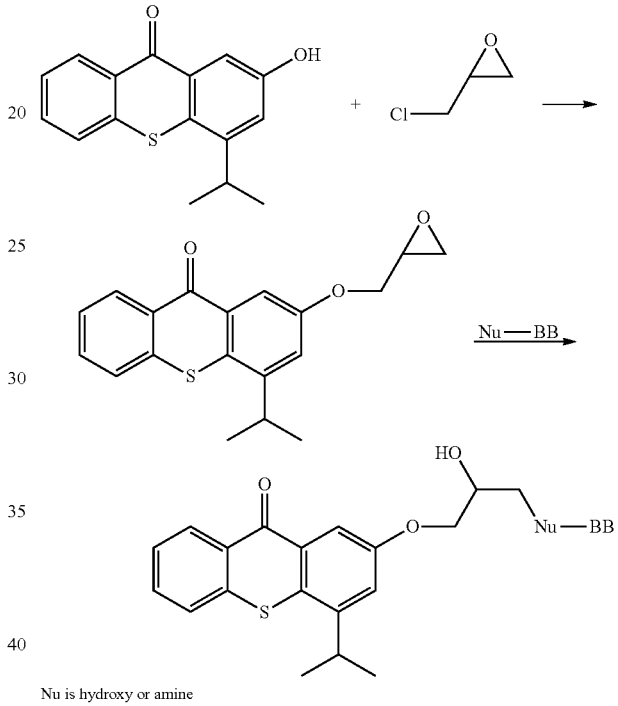

Nu is hydroxy or amine

The spacer unit

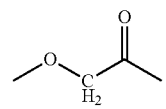

may be conveniently prepared by reaction of a 2-hydroxy thioxanthone derivative with a halo acetic acid derivative, such as bromo acetic acid ethyl ester, and subsequent reaction with a nucleophilic group (Nu) of the backbone unit BB:

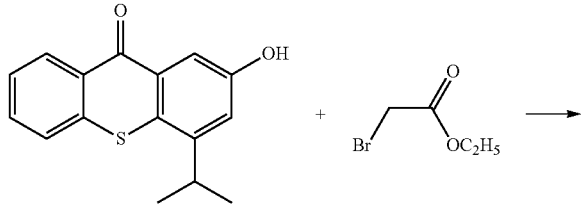

-continued

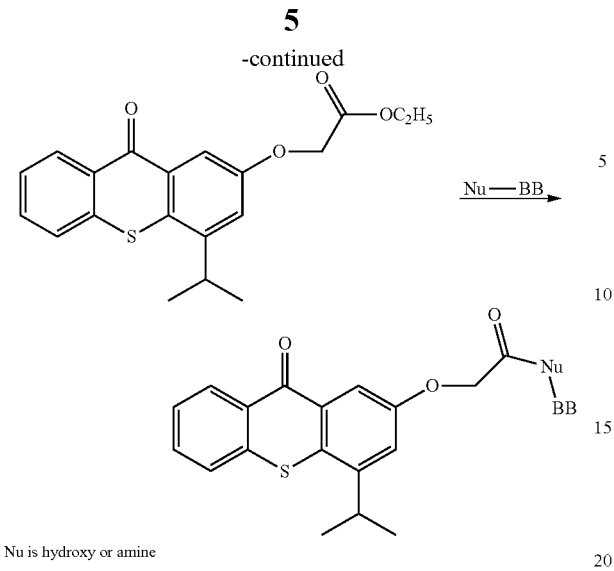

Nu is hydroxy or amine

Also the reaction between an α-halocarboxylic acid derivative and a hydroxy-containing compound is well-known. It is generally carried out under heating in the presence of a base such as sodium hydroxide.

As mentioned above, according to a particularly preferred embodiment of the present invention the backbone unit comprises at least one amine moiety. It has been surprisingly found that such compounds are not only good photoinitiators, which as such was not foreseeable, but that the insertion of such amine groups led to an enhancement of the photoreactivity of the compounds.

According to an especially preferred embodiment of the present invention, such amino group is a tertiary amino group.

A preferred group of compounds of said embodiment is characterized by the formula

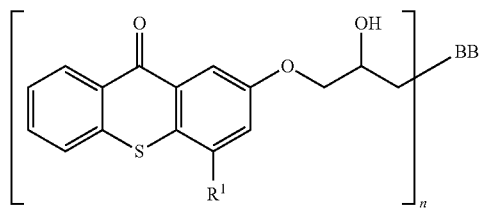

wherein
$R^1$ is H or linear or branched $C_{1-8}$-Alkyl, preferably linear or branched $C_{1-6}$-Alkyl, most preferably $CH_3$, $C_2H_5$, n-$C_3H_7$, i-$C_3H_7$, n-$C_4H_9$, s-$C_4H_9$, t-$C_4H_9$;
BB is selected from the group consisting of

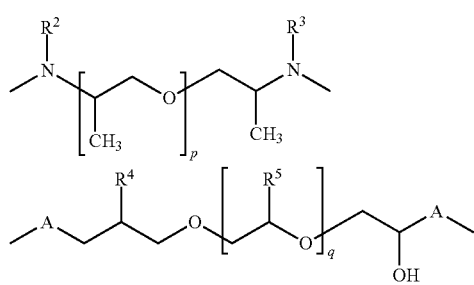

wherein
$R^2$ and $R^3$ are the same or different and denote H or

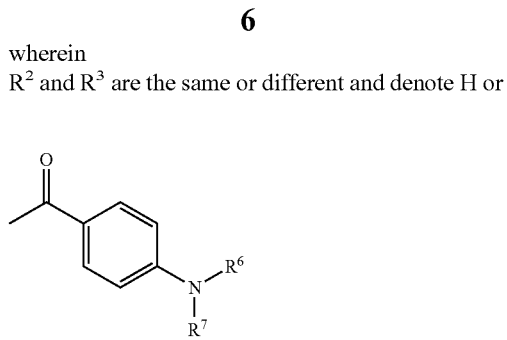

wherein
$R^6$ and $R^7$ are independently H or linear or branched $C_{1-8}$-Alkyl, preferably linear or branched $C_{1-6}$-Alkyl, most preferably $CH_3$, $C_2H_5$, n-$C_3H_7$, i-$C_3H_7$, n-$C_4H_9$, s-$C_4H_9$, t-$C_4H_9$; and
P is an integer from 1 to 10, preferably from 3 to 6, most preferably 3 or 5;
q is an integer from 3 to 12, preferably 9;
A is $NR^B$, wherein $R^8$ is H, a linear or branched $C_{1-4}$ alkyl residue, a $C_{1-4}$ alkylamine residue or

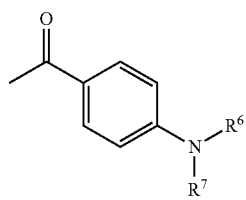

wherein $R^6$ and $R^7$ are as defined above;
$R^4$ is H or Hydroxy;
$R^5$ is H or $CH_3$; and
n is 2.

In this group of compounds, the amine functionality may be present both in the main backbone as well as in side or terminating groups.

The PI-Sp unit to be used here is

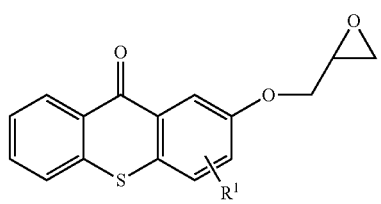

which synthesis has been described above.

The backbone units

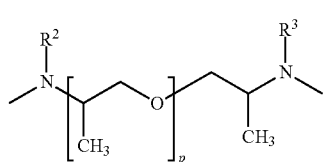

are derived from the commercially available polyoxypropylene amines such as Jeffamine D230 or Jeffamine D400.

The backbone units

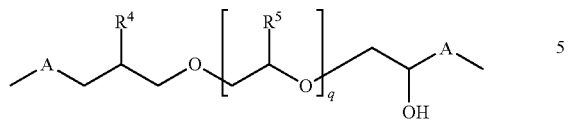

are conveniently prepared by first reacting the amine moiety A with the PI-Sp unit, followed by reaction of the free amino group with e.g. a polyoxyethyleneoxide, as exemplified for the preparation of the following compound:

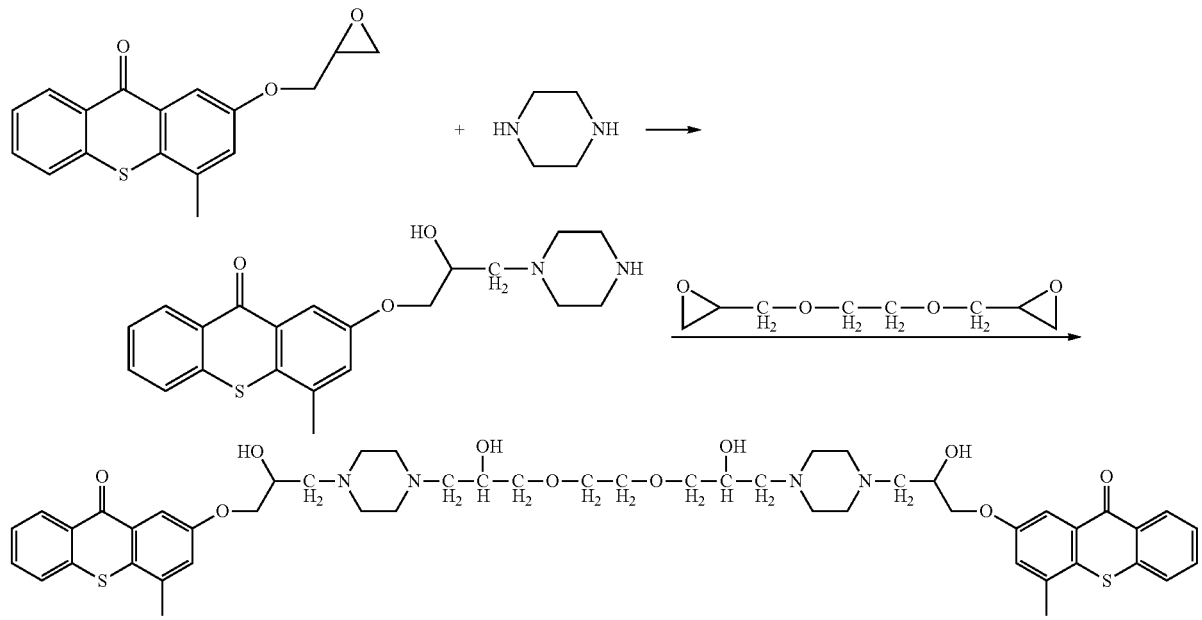

Preferred examples of compounds of this group are:

i)
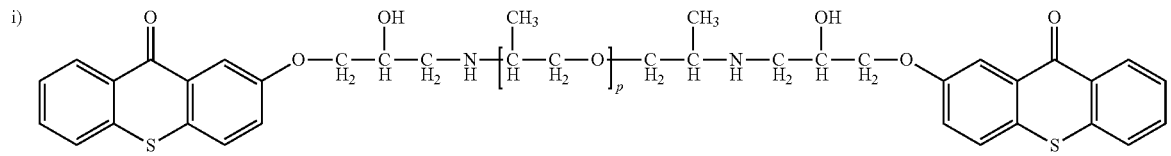
starting material for the backbone: Jeffamine D230 or Jeffamine D400 ii)
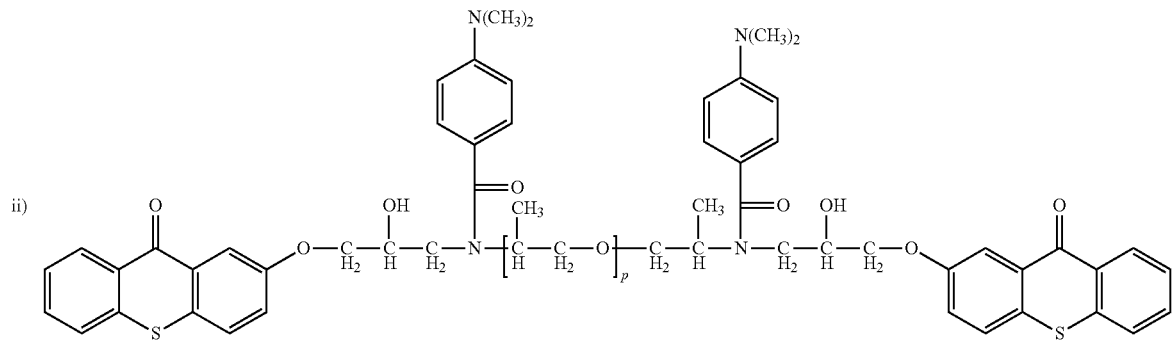
starting material for the backbone: Jeffamine D230 iii) 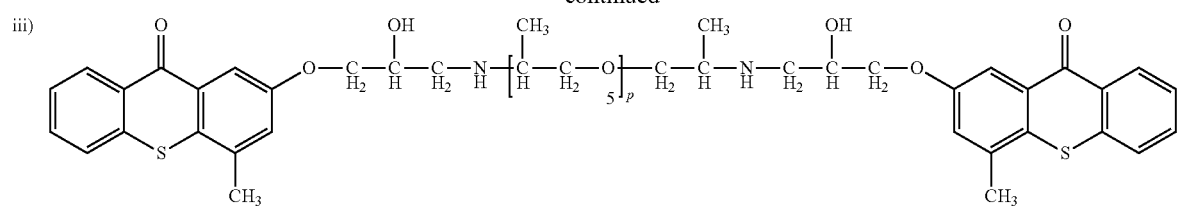
starting material for the backbone: Jeffamine D400
iv) 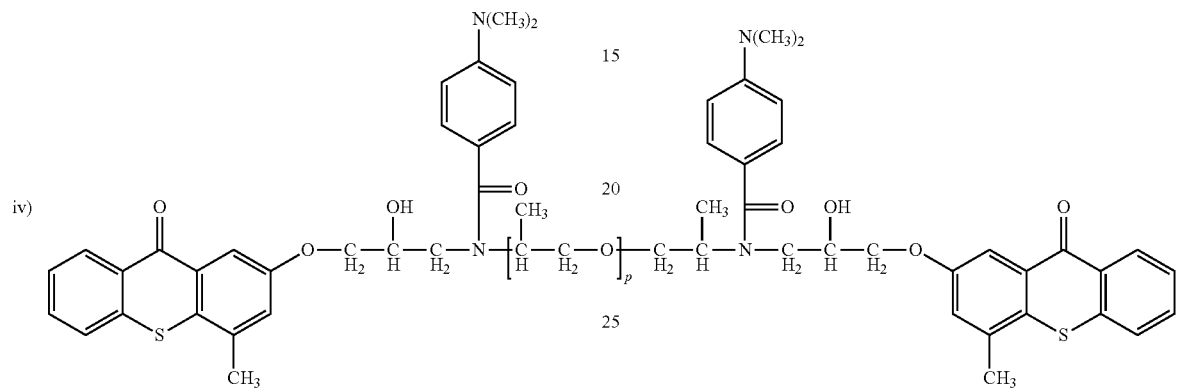
starting material for the backbone: Jeffamine D230
v) 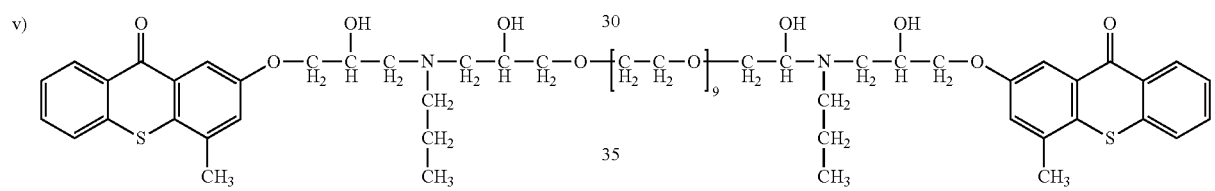
vi) 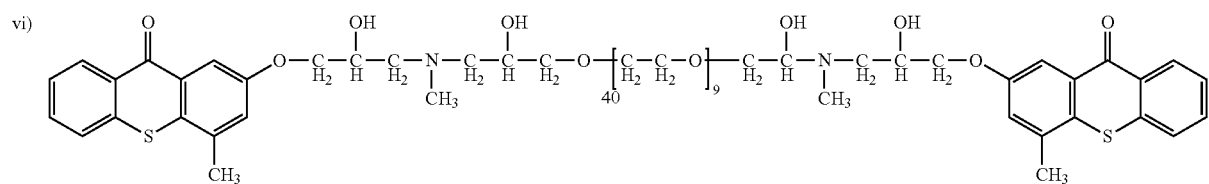
vii) 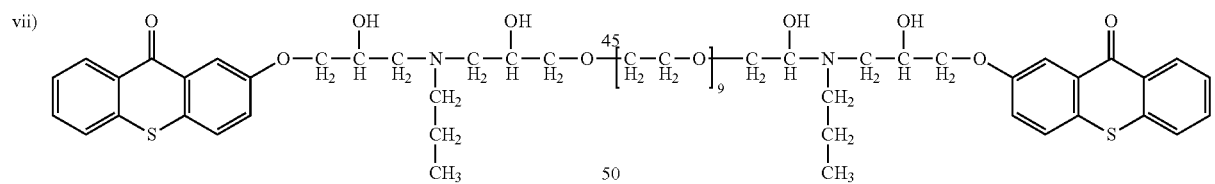
viii) 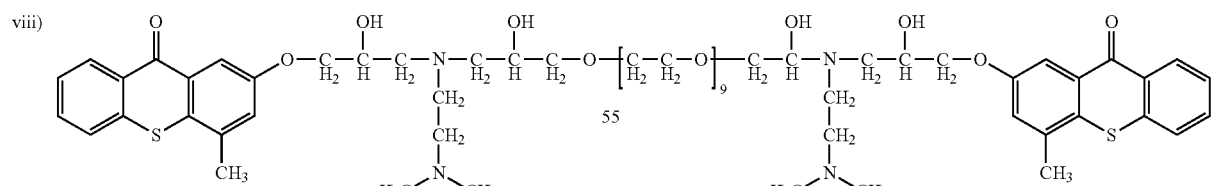
ix) 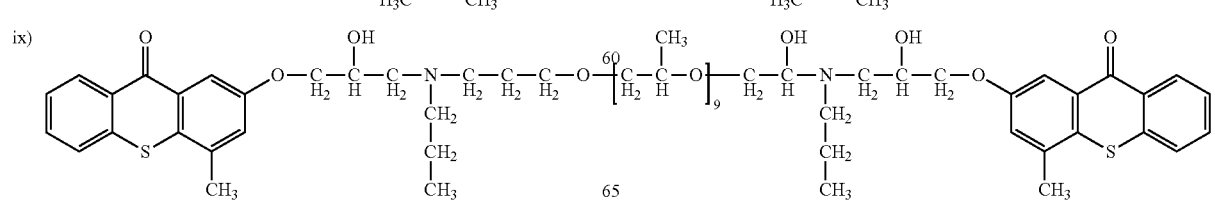

Another preferred group of compounds of the present invention is characterized by the formula

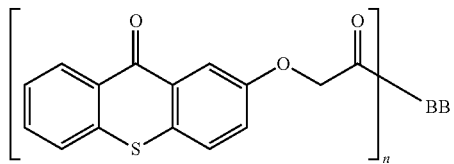

wherein
BB is selected from the group consisting of

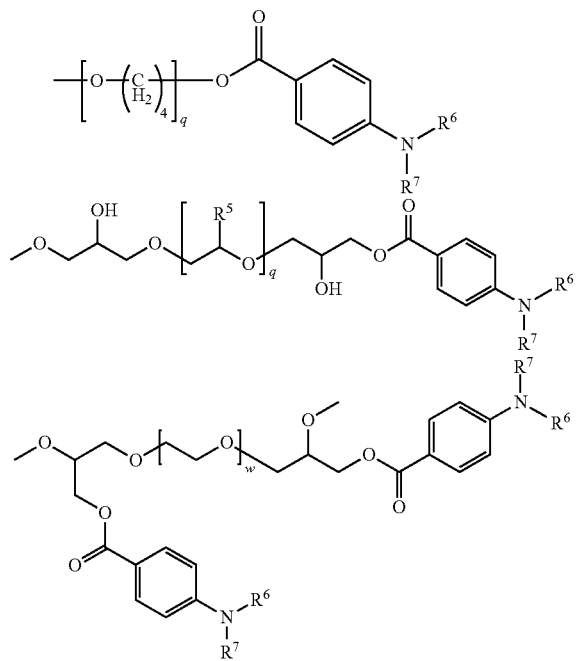

wherein
q is an integer from 3 to 12, preferably 9;
$R^5$ is H or $CH_3$;
$R^6$ and $R^7$ are independently H or linear or branched $C_{1-8}$-Alkyl, preferably linear or branched $C_{1-6}$-Alkyl, most preferably $CH_3$, $C_2H_5$, n-$C_3H_7$, i-$C_3H_7$, n-$C_4H_9$, s-$C_4H_9$, t-$C_4H_9$;
w is an integer from 2 to 15, preferably from 3 to 10.
n is 1 or 2.
The PI-Sp unit to be used here is

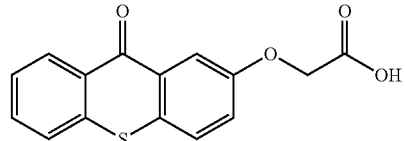

which synthesis has been described above.
The backbone unit

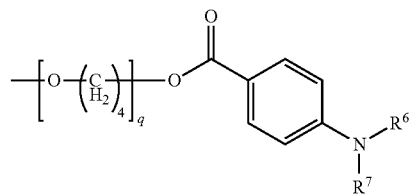

is obtained by reacting the respective PI-Sp unit with a polytetrahydrofurane, and subsequently with a 4-Amino benzoyl derivative.
The backbone unit

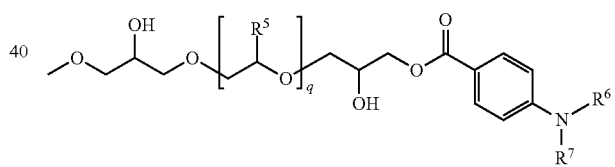

is obtained by reacting the respective PI-Sp unit with a polyoxyethylene diepoxide or polyoxypropylene diepoxide, and subsequently with a 4-Amino benzoyl derivative.
Preferred examples of compounds of this group are:

x)
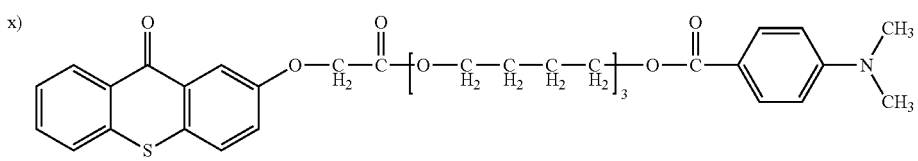

xi)
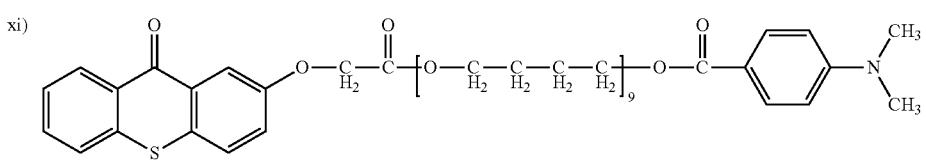

xii)

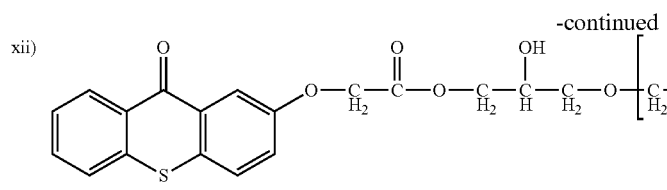

xiii)

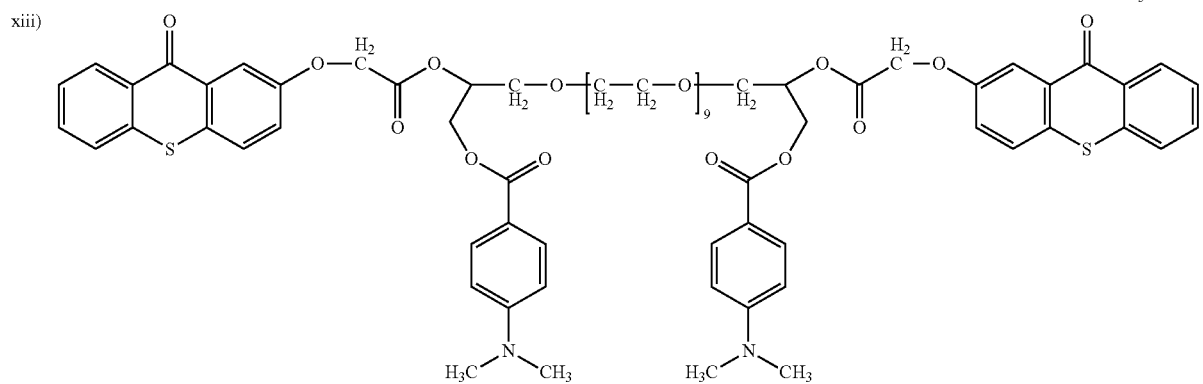

Another preferred group of compounds of the present invention is characterized by the formula

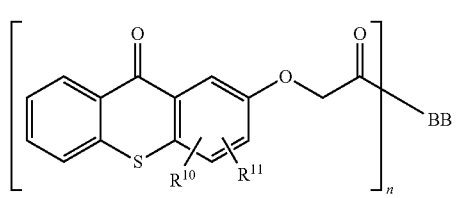

wherein
$R^{10}$ and $R^{11}$ are the same or different and denote H, $CH_3$ or $CH(CH_3)_2$;
BB is selected from the group consisting of

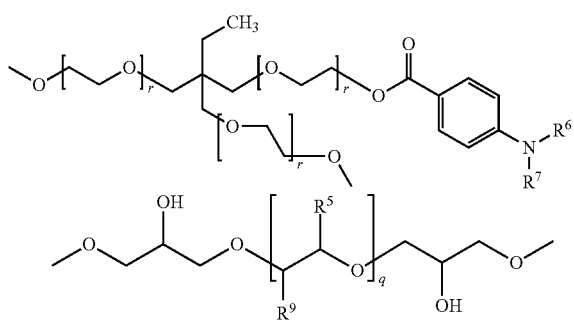

wherein
q is an integer from 3 to 12, preferably 9;
$R^5$ is H or $CH_3$;
$R^6$ and $R^7$ are independently H or linear or branched $C_{1-8}$-Alkyl, preferably linear or branched $C_{1-6}$-Alkyl, most preferably $CH_3$, $C_2H_5$, n-$C_3H_7$, i-$C_3H_7$, n-$C_4H_9$, s-$C_4H_9$, t-$C_4H_9$;
$R^9$ is H or $CH_3$;
r is in the range from 2 to 3;
n is 2.

The PI-Sp unit to be used here is

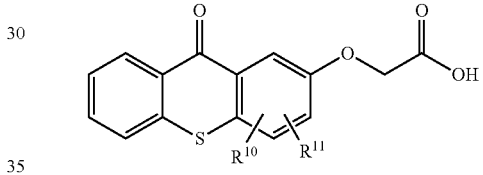

which synthesis has been described above.

In the first backbone of the above list, the polyol is a pentaerythritol-based polyol.

According to the present invention, a pentaerythritol-based polyol is a polyol comprising a quartenary carbon atom and having at least three hydroxy groups. A preferred example is polyol 3380:

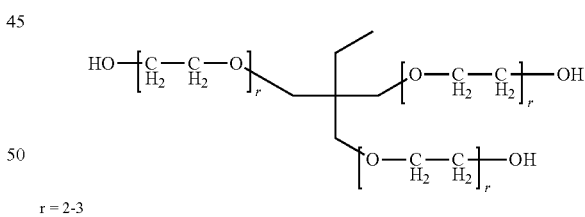

r = 2-3

In the commercial product Polyol 3380, r is statistically 2.5.

Of course, also other polyols having three or more hydroxy groups can be used in a similar way as polyol 3380, in accordance with the present invention.

Depending on the ratio of the starting components, either one, two or all three hydroxy groups of the polyol 3380 may be reacted with the PI-Sp moiety. Remaining free hydroxy groups of the polyol 3380 may be reacted with terminal groups, for example a dialkylaminobenzoyl moiety.

The other backbone unit of the above list is obtained by reacting the respective PI-Sp unit with a polyoxyethylene epoxide or polyoxypropylene epoxide.

Preferred examples of compounds of this group are:

xiv)

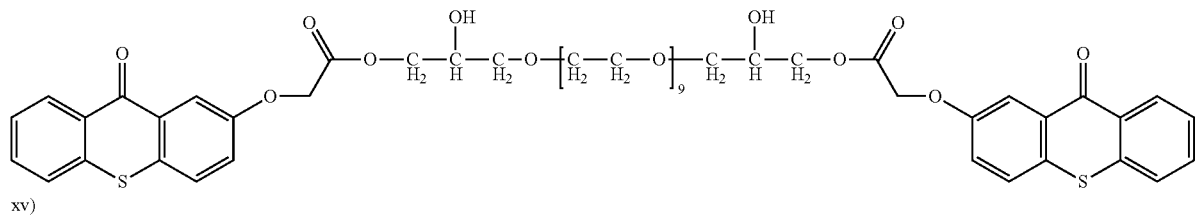

xv)

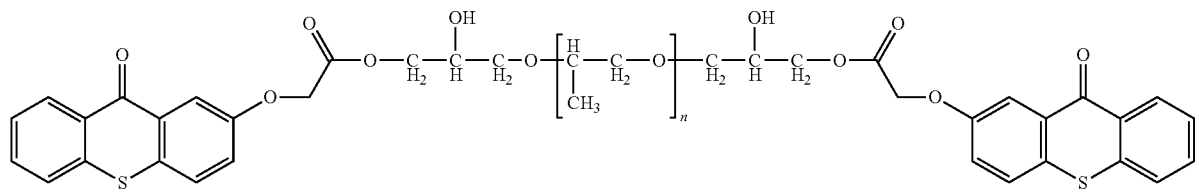

starting material for the backbone: DER 732 (from Dow)

The above described photoinitiators may be added to conventional radiation-curable coating compositions. Such coating compositions are commonly known in the art and need not be reiterated here in detail.

A coating composition incorporating the photoinitiators of the present invention will normally comprise at least one radiation-curable monomer and/or oligomer, a photoinitiators of the present invention and optionally an additional reactive diluent. In the case of a printing ink, the composition will also contain a colorant, e.g. a pigment.

The radiation-curable monomer or oligomer is preferably an ethylenically unsaturated compound. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetraacrylate, di-pentaerythritol pentaacrylate, polyether acrylates, such as ethoxylated trimethylol propane triacrylate, glycerol propoxylate triacrylate, ethoxylated pentaerythritol tetraacrylate, and epoxy acrylates such as dianol diacrylate (=the diacrylate of 2, 2-bis[4-(2-hydroxyethoxy)phenyl]propane, Ebecryl 150 from UCB) and glycol diacrylates such as tripropylene glycol diacrylate.

It is a great benefit of the present invention that the majority of the photoinitiators described herein comprise an amine moiety within its molecule. Thus, the amount of additional synergist can be largely reduced or even for some applications completely be omitted. Therewith, any migration of said small molecule synergist from the final coating is largely reduced, leading to a reduction of environmental problems. However, for the use of photoinitiators of the present invention which do not comprise an amine moiety within the molecule, the compositions of the present intention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used in flexographic printing applications may contain both amine types.

The multi-functional initiators of formula (I) are especially suited for inks, especially printing inks, including lithographic inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference. The photoinitiators of the present invention have shown a good compatibility with the other components of these compositions.

The present invention will now be further described with respect to non-limiting examples.

EXAMPLE 1

Synthesis of Thioxanthone Derivatives

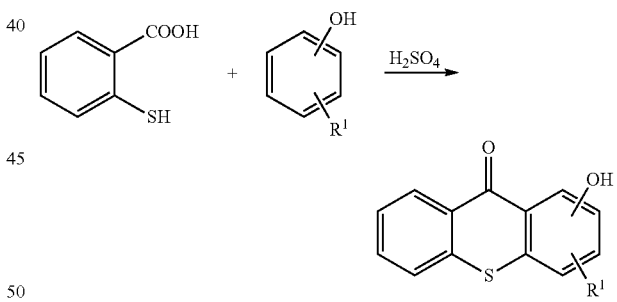

The general process for synthesis of HTX intermediates containing hydroxyl was carried out as follows: Thiosalycylic acid (0.1 mol) was slowly added to 150 ml of concentrated sulfuric acid, and the mixture was stirred for 5 min to ensure thorough mixing. Phenol derivatives (0.5 mol) were added slowly to the stirred mixture over a period of 30 min. After the addition, the reaction mixture was stirred at room temperature for 1 h and then at 80° C. for 2 h, after which it was left to stand at room temperature overnight. The resulting mixture was poured carefully with stirring into a 10-fold excess of boiling water, and was further boiled for 10 min. The solution was cooled and filtered. The residue was recrystallized from dioxane-water. The hydroxy thioxanthones were carefully characterized and confirmed by FT-IR and NMR.

By the above process, the following hydroxy thioxanthones were obtained:

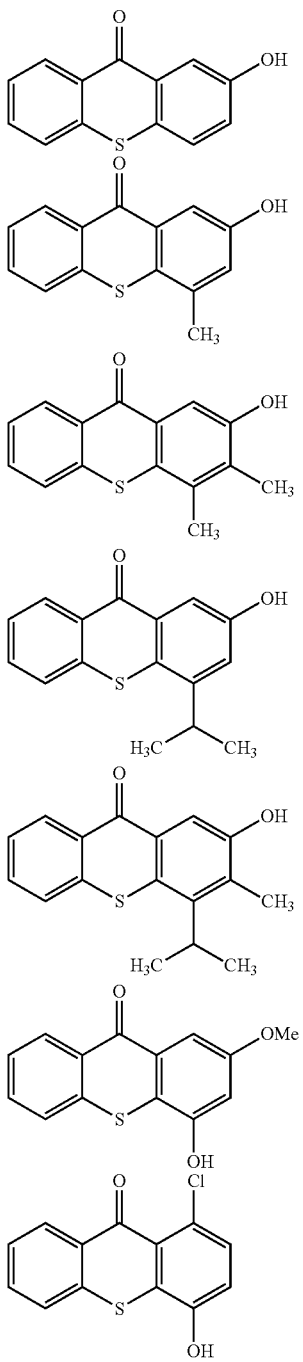

EXAMPLE 2

Preparation of PI-SP Units

EXAMPLE 2a

Acid-Thioxanthone Intermediates

The synthesis of Acid-Thioxanthone intermediates is shown in an exemplary way on the synthesis of 4-Isopropyl-2-carboxymethyloxy-thioxanthone:

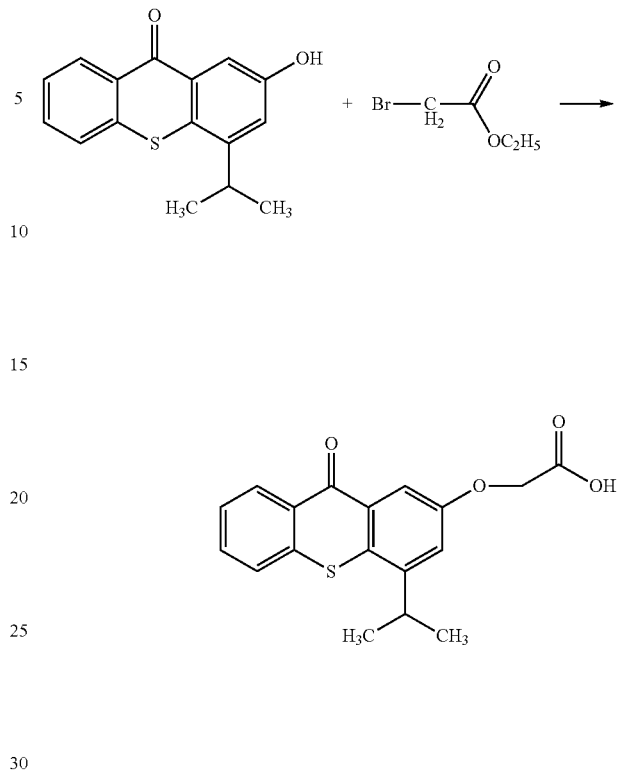

2.4 g sodium hydroxide was refluxed in 40 ml tetrahyrofuran (THF) for 5 min. 4-Isopropyl-2-hydroxy thioxanthone (2.7 g, 0.01 mol) was added and reflux was continued for 1 h, during which time the colour changed to red, indicating the formation of the sodium salt of 4-Isopropyl-2-hydroxy thioxanthone. Ethyl bromoacetate (3.51 g, 0.021 mol) was added and reflux was continued for 5 h, wherein the colour of the solution changed into yellow. After cooling to room temperature, 40 ml water was added, and the THF was distilled out to yield a clear red solution. The solution was refluxed for further 3 h in order to hydrolyse all the ester intermediate. The solution was then cooled to 50° C., and 40 ml 1.0 M hydrochloric acid was added, causing the solid product to precipitate out. After refluxing for a further 10 min to be sure that all the sodium salt was converted to the free acid, the solution was cooled to room temperature and stirred for 2 h before filtering off the solid, washing with 40 ml water and drying in vacuum oven at 80° C. The yield was about 95%.

The other used Acid-Thioxanthone intermediates were obtained in the same way starting from the respective thioxanthone derivative.

EXAMPLE 2b

2-Carboxymethyloxy Thioxanthone

2-Carboxymethyloxy thioxanthone can be synthesized by a one-step reaction: Thiosalycylic acid (0.1 mol) was slowly added to 150 ml of concentrated sulfuric acid, and the mixture was stirred for 5 min to ensure thorough mixing. Phenoxy acetic acid (0.5 mol) were added slowly to the stirred mixture over a period of 30 min. After the addition, the reaction mixture was stirred at room temperature for 1 h and then at 80° C. for 2 h, after which it was left to stand at room temperature overnight. The resulting mixture was poured carefully with stirring into a 10-fold excess of boiling water,

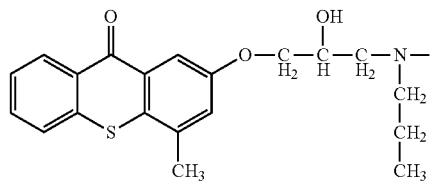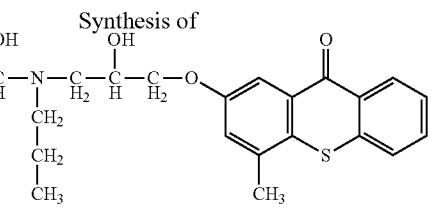

and was further boiled for 10 min. The solution was cooled and filtered. The residue was recrystallized from dioxane-water.

EXAMPLE 2c

Epoxy-Thioxanthone Intermediates

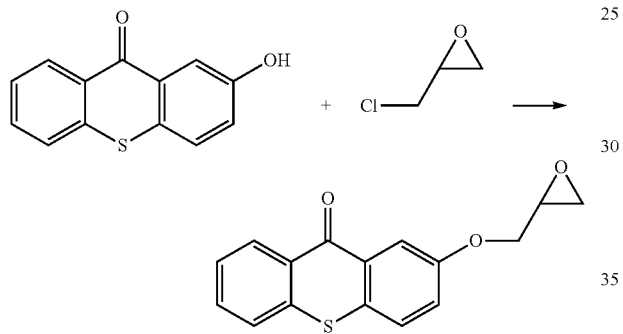

The general process for synthesis of epoxy-thioxanthone intermediates was as follows: A mixture of hydroxyl thioxanthone (0.03 mol), epichlorohydrin (20 ml), anhydrous potassium carbonate powder (6.5 g), toluene (30 ml), and polyethylene glycol (PEG-400, 0.5 ml), was stirred for 2 h at 80° C. and then refluxed for 2 h at 135° C. The organic layer was poured out after cooling, and the inorganic residue was washed with toluene until the solution became colourless. The combined solution was distilled to remove the solvent and excessive epichlorohydrin, and the residue was distributed between chloroform and water in a separating funnel. The chloroform solution was dried over anhydrous calcium chloride and evaporated. The crude product was recrystallized from ethanol-toluene (V/V=6/1).

The other used Epoxy-Thioxanthone intermediates were obtained in the same way starting from the respective thioxanthone derivative.

EXAMPLE 3

Preparation of Photoinitiators

EXAMPLE 3.1

Synthesis of 0.01 mol 4-methyl-2-epoxymethyloxy thioxanthone (obtained in accordance with example 2c) and 0.04 mol propylamine (PA) were dissolved in 20 ml chloroform, and the mixture was stirred at 40° C. for 12 hours. Unreacted PA and the solvent chloroform were removed by rotary evaporation, to obtain 4-methyl-2-(1-propyl-amino-2-hydroxy)-propoxy thioxanthone (4M2ETX-PA). 0.005 mol PE0526 (Polyoxyethylene diepoxide) and 40 ml ethanol were added into flask containing 4M2ETX-PA. The mixture was refluxed at 80° C. for 8 hours under $N_2$ atmosphere. The solvent ethanol was removed by rotary evaporation, to obtain the title compound.

In a similar manner, by using other amine compounds such as piperazine further photoinitiators comprising amine moieties within the backbone could be generated.

In the case of using polymeric amines like Jeffamines, it was not necessary to add an polyalkoxy compound.

EXAMPLE 3.2

Synthesis of

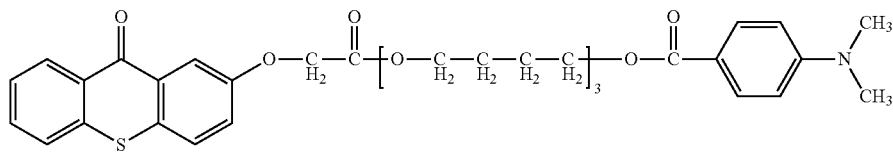

2-Carboxymethyloxy thioxanthone (2.88 g, 0.01 mol, obtained in accordance with example 2b), p-THF 650 (6.50 g, 0.01 mol), 4-dimethylaminobenzoic acid (2 g, 0.012 mol), 0.3 g p-toluene sulphonic acid and 100 ml xylene were added into a three-necked flask equipped with a nitrogen inlet, and a Dean-Stark trap. The mixture solution was azeotropically distilled at 150° C. for 12 h, and then xylene was distilled off. The mixture was heated to 200° C. for 5 h and then cooled to 80° C. Subsequently, 100 ml toluene was added with stirring. The solution was cooled to room temperature, then filtered, and washed twice with 100 ml 0.25M sodium hydroxide and twice with 100 ml water. The organic phase was dried over anhydrous magnesium sulphate and all solvent was removed using a rotary evaporator to yield a red oil. The yield was about 86%.

In a similar manner, by using other polyalkoxy compounds compounds such as polyoxyethylene diepoxide or poyloxypropylene diepoxide, further photoinitiators comprising terminal amine moieties could be generated.

In the case of using polymeric amines like Jeffamines, it was not necessary to add an polyalkoxy compound.

EXAMPLE 3.3

Synthesis of

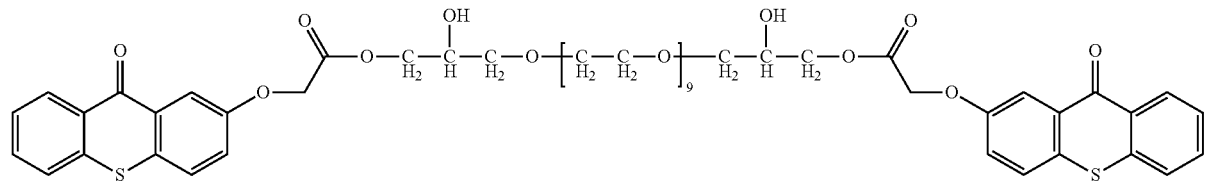

0.2 mol 2-Carboxymethyloxy thioxanthone (obtained in accordance with example 3b) and 0.1 mol PEO 526 (Polyoxyethylene diepoxide) were added into a flask. The mixture was heated to 150° C. for 12 h, and then to 180° C. for 6 h, to obtain the title compound. The yield was about 100%.

EXAMPLE 3.4

Synthesis of

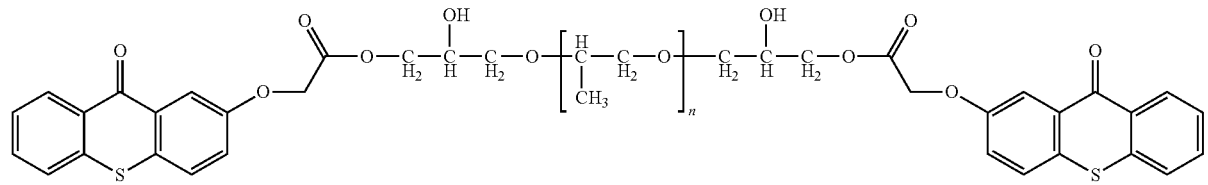

This compound was synthesized in a similar manner as in example 3.3, but using DER 732 epoxy resin from Dow instead of PEO 526.

It is understood that the other compounds of the present invention may be prepared in a similar manner by using respective starting or intermediate materials. Optional slight variations of the reaction conditions are within the common routine of the skilled person.

Derivatization reactions (such as esterifying free hydroxy groups or amidifying free amino groups) can be carried out by standard procedures which need not be described in detail here.

EXAMPLE 4

Preparation of a Printing Ink a) Ink with Amine-Containing Photoinitiator

A printing ink was prepared by mixing, in a conventional manner, the following components:

| Component | Wt.-% |
|---|---|
| Ebecryl 657 (Polyester Acrylate) | 30 |
| Ebecryl 1608 (Epoxy Acrylate) | 22.3 |
| TMPTA (Monomer) | 20 |
| Photoinitiator (example 3.2) | 8 |

-continued

| Component | Wt.-% |
|---|---|
| Speedcure EDB (Ethyl Di methyl amino benzoate, synergist) | 1.2 |
| Florstab UV 1 (Stabiliser) | 0.5 |
| Ciba Irgalite GLO (Pigment, PB 15:3) | 18 |

The ink exhibited good curing properties without the need of using an additional amine synergist.

b) Ink without Amine-Containing Photoinitiator

A printing ink was prepared by mixing, in a conventional manner, the following components:

| Component | Wt.-% |
|---|---|
| Ebecryl 657 (Polyester Acrylate) | 30 |
| Ebecryl 1608 (Epoxy Acrylate) | 23.5 |
| TMPTA (Monomer) | 20 |
| Photoinitiator (example 3.3) | 4 |
| Speedcure EDB (Ethyl Di methyl amino benzoate, synergist) | 4 |
| Florstab UV 1 (Stabiliser) | 0.5 |
| Ciba Irgalite GLO (Pigment, PB 15:3) | 18 |

The ink exhibited good curing properties.

Test Procedures a) Film Alcohol Resistance Test

On a plastic substrate, a standard sample is provided next to a sample of a coating composition of the present invention. The curing is carried out with a mercury bulb (160 W/cm, speed of conveyer 30 m/min). A side by side draw down is carried out on a plastic film, including the standard and the test ink. With a cotton soaked with alcohol, the ink film is treated until disappearance. The number of double rubs which are necessary in this respect give the level of curing.

b) Curing Limit

A ink of the present invention is printed on a plastic substrate with a Little Joe or PrüfBau machine, at 1.50 g/m². Several pieces of the print are cut. Each piece is passed in the UV dryer with a conveyor speed decreasing step by step at each sample. It is evaluated with a thumb turn whether the film is cured or not. If not, the speed is reduced, and another piece of print is passed and evaluated again in curing. As the speeds is reduced, the irradiation becomes sufficient to have the ink fully cured, and the thumb does not leave a mark on the print anymore. The speed of the dryer is then recorded, and taken as the "curing limit" (m/min). The higher the figure, the higher the reactivity of the ink.

In the following table, the results of the curing limit test for several inks of the present invention comprising various photoinititiators of the present invention as compared to the reference product Omnipol TX (WO 03/033492, ex. 3) are given. The inks were prepared in accordance with example 4 (the ink according to comparative example 1 (C1) was prepared according to example 4b, using 3 wt.-% Omnipol TX and accordingly 24.5 wt.-% Ebecryl 1608):

under pressure (10 tons) at room temperature for 30 seconds. The results are expressed in function of the blocking scale and provides an assessment of the surface cure.

d) Reactivity Towards Isocyanate-Terminated Polyurethanes

In order to show that certain inks of the present invention which exhibit free hydroxyl groups may be grafted onto suitable binder resins, an ink according to example 4b), but comprising the photoinitiator according to example 3.4 was added to a polyurethane comprising free terminal isocyanate groups. After a reaction time of 2 h at 70° C., a marked decrease of free isocyanate groups could be observed.

A similar ink but comprising Omnipol TX did not, under the same conditions, react with said polyurethane comprising free terminal isocyanate groups.

The invention claimed is:

1. Photoinitiators of the formula (I)

$$(PI\text{-}Sp)_n\text{-}BB \qquad (I)$$

wherein

PI is a thioxanthone moiety optionally comprising additional substituents further to the Sp moiety

| Ink no. | Photoinitiator in ink | Curing limit (m/min) |
|---|---|---|
| C1 | Omnipol TX | 130 |
| |  | |
| 1 | | 150 |
| 2 | | 140 |

It was shown that the inks of the present invention showed a comparable or even better curing limit value than the reference example Omnipol TX. Moreover, in the case of example 1 the amount of additional synergist could be significantly reduced, which lowered migration problems caused by the synergist.

c) Blocking Test

Drawdown of an ink of the present invention versus a standard is conducted on a porous paper (paper printer). The curing parameter is: 1 pass 120 m/min 1 lamp min power. The print is maintained versus a blank piece of the porous paper Sp is a spacer unit which is selected from the group consisting of

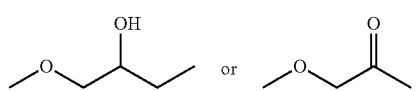

BB is a backbone moiety selected from the group consisting of r is in the range from 2 to 3;
w is an integer from 2 to 15, preferably from 3 to 10; and
n is 1 or 2.

2. Photoinitiators according to claim 1, wherein the SP moiety is linked to the 2 position of the PI thioxanthone moiety.

3. Photoinitiators according to claim 1, wherein the moiety PI is substituted with at least one residues selected from the group consisting of linear or branched $C_{1-8}$ alkyl, linear or branched $C_{1-8}$ alkoxy, or halogen.

4. Photoinitiators according to claim 3, wherein in 4-position of the PI moiety there is a linear or branched $C_{1-8}$ alkyl residue.

5. Photoinitiators according to one claim 1, having the formula wherein
$R^1$ is H or linear or branched $C_{1-8}$-Alkyl;
BB is selected from the group consisting of wherein
$R^2$ and $R^3$ are the same or different and denote H or wherein
$R^2$ and $R^3$ are the same or different and denote H, an optionally substituted linear or branched $C_{1-8}$ alkyl residue or an acyl residue;
$R^4$ is H or Hydroxy
$R^5$ is H or $C_{1-4}$-Alkyl;
$R^6$ and $R^7$ are the same or different and denote H or an optionally substituted linear or branched $C_{1-8}$ alkyl residue;
A is $NR^8$, wherein
$R^8$ is H, an optionally substituted linear or branched $C_{1-8}$ alkyl residue, or an optionally substituted $C_{1-8}$ alkylamine residue;
$R^9$ is H or $C_{1-4}$-Alkyl;
p is an integer from 1 to 10, preferably from 3 to 6;
q is an integer from 3 to 12;

wherein
$R^6$ and $R^7$ are independently H or linear or branched $C_{1-8}$-Alkyl; and
p is an integer from 1 to 10;
q is an integer from 3 to 12;
A is $NR^8$, wherein $R^8$ is H, a linear or branched $C_{1-4}$ alkyl residue, a $C_{1-4}$ alkylamine residue or

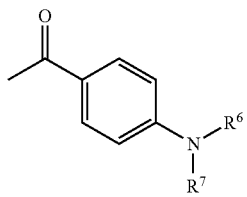

wherein $R^6$ and $R^7$ are as defined above;
$R^4$ is H or Hydroxy;
$R^5$ is H or $CH_3$; and
n is 2.

6. Photoinitiators according to claim 1, having the formula

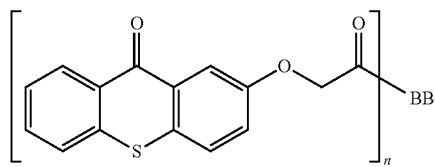

wherein
BB is selected from the group consisting of

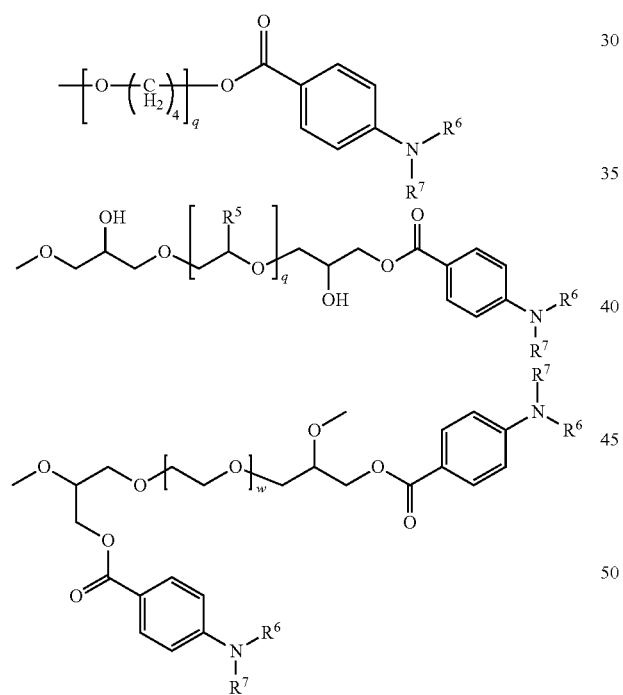

wherein
q is an integer from 3 to 12;
$R^5$ is H or CH—;
$R^6$ and $R^7$ are independently H or linear or branched $C_{1-8}$-Alkyl;
w is an integer from 2 to 15;
n is 1 or 2.

7. Photoinitiators according to claim 1, having the formula

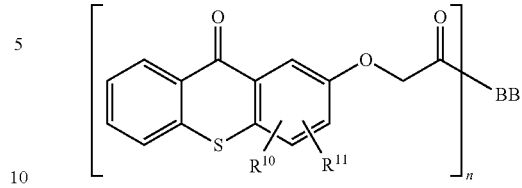

wherein
$R^{10}$ and $R^{11}$ are the same or different and denote H, $CH_3$ or $CH(CH_3)_2$;
BB is selected from the group consisting of

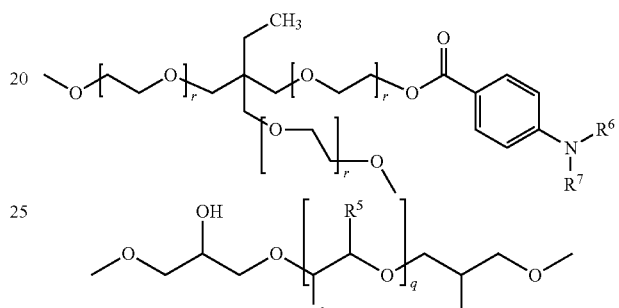

wherein
q is an integer from 3 to 12;
$R^5$ is H or $CH_3$;
$R^6$ and $R^7$ are independently H or linear or branched $C_{1-8}$-Alkyl;
$R^9$ is H or $CH_3$;
r is in the range from 2 to 3;
n is 2.

8. A process for preparing photoinitiators according to claim 1, comprising the steps of
   a) reacting an optionally substituted thioxanthone moiety, wherein the thioxanthone moiety comprises at least one hydroxy group, with a compound selected from the group consisting of epichlorohydrine and halo acetic acid esters,
   b) reacting the intermediate obtained in step a) with a respective backbone unit comprising a functional group capable of reacting with said intermediate from step a), or alternately by first reacting the intermediate obtained in step a) with a compound comprising a functional group capable of reacting with said intermediate from step a), and subsequently reacting the thus obtained intermediate with a respective backbone unit;
   c) optionally derivatizing the compound obtained in step b).

9. A coating composition, comprising a polymerizable component and at least one photoinitiator according to claim 1.

10. Method for the curing of a coating composition, comprising the step of adding a photoinitiator according to claim 1 to said coating composition and subsequently curing said composition.

* * * * *